United States Patent [19]

Hartman et al.

[11] Patent Number: 5,246,847
[45] Date of Patent: Sep. 21, 1993

[54] POLYPEPTIDE ANALOGS OF HUMAN MANGANESE SUPEROXIDE DISMUTASE AND COMPOSITIONS AND COMPLEXES THEREOF

[75] Inventors: Jacob R. Hartman, Holon; Yaffa Beck, Gadera, both of Israel

[73] Assignee: Bio-Technology General Corp., New York, N.Y.

[21] Appl. No.: 842,740

[22] Filed: Feb. 27, 1992

Related U.S. Application Data

[63] Continuation of Ser. No. 449,090, Dec. 8, 1989, abandoned, which is a continuation of Ser. No. 907,051, Sep. 12, 1986, abandoned, which is a continuation-in-part of Ser. No. 801,090, Nov. 22, 1985, abandoned.

[51] Int. Cl.⁵ .................. C12N 9/02; A61K 37/50
[52] U.S. Cl. ........................... 435/189; 424/94.4
[58] Field of Search ............... 435/189, 172.3; 424/94.4

[56] References Cited

U.S. PATENT DOCUMENTS 4,517,294  5/1985  Bock et al. .................. 435/69.4
4,751,180  6/1988  Cousens et al. ................. 435/68

OTHER PUBLICATIONS

Freifelder, D., Molecular Biology (Jones & Bartlett Publishers, Boston, MA) pp. 826-833 (1983).
Stryer, L., Biochemistry, W. H. Freeman and Co., San Francisco p. 18 (1975).
Coombs, J., Dictionary of Biotechnology, Elsevier, New York p. 248 (1986).
Steinman, H. M., Superoxide Dismutase (Oberly, ed.), CRC Press, Florida pp. 11-68.
Barra, D. et al., FEBS Letters 120: 53-56 (1980).
Joe M. McCord and Irwin Fridovich, Superoxide Dismutase, *J. Biol. Chem.* 224(22): 6049-6055 (1969).
Stryer, L., Biochemistry, W. H. Freeman and Co., San Francisco, CA p. 30 (1975).
Barra et al. *J. Biol. Chem.* 259: 12595-12601, 1984.

*Primary Examiner*—Richard A. Schwartz
*Assistant Examiner*—Robert A. Hodges
*Attorney, Agent, or Firm*—John P. White

[57] ABSTRACT

A double-stranded cDNA molecule which includes DNA encoding human manganese superoxide dismutase has been created. The sequence of one strand of a double-stranded DNA molecule which encodes human maganese superoxide dismutase has been discovered. Such molecules may be introduced in procaryotic, e.g., bacterial, or eukaryotic, e.g., yeast or mammalian, cells and the resulting cells cultured or grown under suitable conditions so as to produce human manganese superoxide dismutase or analogs thereof which may then be recovered. Human MnSOD or analogs thereof may be used to catalyze the reduction of superoxide radicals, reduce reperfusion injury, prolong the survival time of isolated organs, or treat inflammations.

The invention also concerns a method of producing enzymatically active human manganese superoxide dismutase or an analog thereof in a bacterial cell which contains and is capable of expressing a DNA sequence encoding the superoxide dismutase by maintaining the bacterial cell under suitable conditions and in a suitable production medium. The production medium is supplemented with an amount of $Mn^{++}$ so that the concentration of $MN^{++}$ in the medium is greater than about 2 ppm.

This invention also concerns a method of recovering purified enzymatically active manganese superoxide dismutase from bacterial cells.

5 Claims, 5 Drawing Sheets

FIGURE 1A

```
GAATTCGGCG GCGGCATCAG CGGCTAAGCC AGCACTAGCA GC ATG TTG AGC CGG              54
                                                 Met Leu Ser Arg
                                                  1

GCA GTG TGC GGC ACC AGC AGG CAG AAG CTG GCT CCG GCT TTG GGG TAT CTG        102
Ala Val Cys Gly Thr Ser Arg Gln Lys Leu Ala Pro Ala Leu Gly Tyr Leu
 5                   10                      15                    20

GGC TCC AGG CAG AAG CAC AGC CTC CCC GAC CTG CCC TAC GAC TAC GGC            150
Gly Ser Arg Gln Lys His Ser Leu Pro Asp Leu Pro Tyr Asp Tyr Gly
             25                      30                      35

GCC CTG GAA CCT CAC ATC AAC GCG CAG ATC ATG CAG CTG CAC CAC AGC            198
Ala Leu Glu Pro His Ile Asn Ala Gln Ile Met Gln Leu His His Ser
        40                      45                      50

AAG CAC CAC GCG GCC TAC GTG AAC CTG AAC GTC ACC GAG GAG AAG                246
Lys His His Ala Ala Tyr Val Asn Leu Asn Val Thr Glu Glu Lys
             55                      60                      65

TAC CAG GAG GCG TTG GCC AAG GGA GAT GTT ACA GCC CAG ATA GCT CTT            294
Tyr Gln Glu Ala Leu Ala Lys Gly Asp Val Thr Ala Gln Ile Ala Leu
70                      75                      80

CAG CCT GCA CTG AAG TTC AAT GGT GGT CAT ATC AAT CAT AGC ATT                342
Gln Pro Ala Leu Lys Phe Asn Gly Gly His Ile Asn His Ser Ile
85                      90                      95                    100

TTC TGG ACA AAC CTC AGC CCT AAC GGT GGT GGA GAA CCC AAA GGG GAG            390
Phe Trp Thr Asn Leu Ser Pro Asn Gly Gly Gly Glu Pro Lys Gly Glu
             105                     110                     115
```

FIGURE 1B

```
TTG CTG GAA GCC ATC AAA CGT GAC TTT GGT TCC TTT GAC AAG TTT AAG       438
Leu Leu Glu Ala Ile Lys Arg Asp Phe Gly Ser Phe Asp Lys Phe Lys
120                         125                         130

GAG AAG CTG ACG GCT GCA TCT GTT GGT GTC CAA GGC TCA GGT TGG GGT       486
Glu Lys Leu Thr Ala Ala Ser Val Gly Val Gln Gly Ser Gly Trp Gly
135                         140                         145

TGG CTT GGT TTC AAT AAG CAA CGG GGA CAC TTA CAA ATT GCT GCT TGT       534
Trp Leu Gly Phe Asn Lys Gln Arg Gly His Leu Gln Ile Ala Ala Cys
150                         155                         160

CCA AAT CAG GAT CCA CTG CAA GGA ACA ACA GGC CTT ATT CCA CTG CTG       582
Pro Asn Gln Asp Pro Leu Gln Gly Thr Thr Gly Leu Ile Pro Leu Leu
165                         170                         175                         180

GGG ATT GAT GTG TGG GAG CAC GCT TAC TAC CTT CAG TAT AAA AAT GTC       630
Gly Ile Asp Val Trp Glu His Ala Tyr Tyr Leu Gln Tyr Lys Asn Val
185                         190                         195

AGG CCT GAT TAT CTA AAA GCT ATT TGG AAT GTA ATC AAC TGG GAG AAT       678
Arg Pro Asp Tyr Leu Lys Ala Ile Trp Asn Val Ile Asn Trp Glu Asn
200                         205                         210

GTA ACT GAA AGA TAC ATG GCT TGC AAA AAG TAAACCACGA TCGTTATGCT         728
Val Thr Glu Arg Tyr Met Ala Cys Lys Lys
215                         220

GATCATACCC TAATGATCCC AGCAAGATAA TGTCCTGTCT TCTAAGATGT GCATCAAGCC     788

TGGTACATA CTGAAACCCC GAATT                                            813
```

POLYPEPTIDE ANALOGS OF HUMAN MANGANESE SUPEROXIDE DISMUTASE AND COMPOSITIONS AND COMPLEXES THEREOF

This application is a continuation of U.S. Ser. No. 449,090, filed Dec. 8, 1989, now abandoned, which is a continuation of U.S. Ser. No. 907,051, filed Sep. 12, 1986, now abandoned, which was a continuation-in-part of U.S. Ser. No. 801,090, filed Nov. 22, 1985, now abandoned.

BACKGROUND OF THE INVENTION

Throughout this application, various publications are referenced by arabic numerical within parentheses. Full citations for these references may be found at the end of the specification immediately preceding the claims. The disclosures of these publications in their entireties are hereby incorporated by reference into this application in order to more fully described the state of art as known to those skilled therein as of the date of the invention described and claimed herein.

Superoxide dismutase (SOD) and the phenomenon of oxygen free radicals ($O_2^-$) was discovered in 1968 by McCord and Fridovich (1). Superoxide radicals and other highly reactive oxygen species are produced in every respiring cell as by-products of oxidative metabolism, and they have been shown to cause extensive damage to a wide variety of macromolecules and cellular components (for review see 2,3). A group of metalloproteins known as superoxide dismutases catalyze the oxidation-reduction reaction $2O_2^- + 2H^+ \rightarrow H_2O_2 + O_2$ and thus provide a defense mechanism against oxygen toxicity.

There are several known forms of SOD containing different metals and different proteins. Metals present in SOD include iron, manganese, copper and zinc. All of the known forms of SOD catalyze the same reaction. These enzymes are found in several evolutionary groups. Superoxide dismutases containing iron are found primarily in prokaryotic cells. Superoxide dismutases containing copper and zinc have been found in virtually all eukaryotic organisms (4). Superoxide dismutases containing manganese have been found in organisms ranging from microorganisms to man.

Since every biological macromolecule can serve as a target for the damaging action of the abundant superoxide radical, interest has evolved in the therapeutic potential of SOD. The scientific literature suggests that SOD may be useful in a wide range of clinical applications. These include prevention of oncogenesis and of tumor promotion, and reduction of the cytotoxic and carditoxic effects of anticancer drugs (10), protection of ischemic tissues (12) and protection of spermatozoa (13). In addition, there is interest in studying the effect of SOD on the aging process (14).

The exploration of the therapeutic potential of human SOD has been limited mainly due to its limited availability.

Superoxide dismutase is also of interest because of its anti-inflammatory properties (11). Bovine-derived superoxide dismutase (orgotein) has been recognized to possess anti-inflammatory properties and is currently marketed in parts of Europe as a human pharmaceutical. It is also sold in the United States as a veterinary product, particularly for the treatment of inflamed tendons in horses. However, supplies of orgotein are limited. Prior techniques involving recovery from bovine or other animal cells have serious limitations and the orgotein so obtained may produce allergic reactions in humans because of its non-human origin.

Copper zinc superoxide dismutase (CuZn SOD) is the most studied and best characterized of the various forms of superoxide dismutase.

Human CuZn SOD is a dimeric metallo-protein composed of identical non-covalently linked subunits, each having a molecular weight of 16,000 daltons and containing one atom of copper and one of zinc (5). Each subunit is composed of 153 amino acids whose sequence has been established (6,7).

The cDNA encoding human CuZn superoxide dismutase has been cloned (8). The complete sequence of the cloned DNA has also been determined (9). Moreover, expression vectors containing DNA encoding superoxide dismutase for the production and recovery of superoxide dismutase in bacteria have been described (24,25). The expression of a superoxide dismutase DNA and the production of SOD in yeast has also been disclosed (26).

Recently, the CuZn SOD gene locus on human chromosome 21 has been characterized (27) and recent developments relating to CuZn superoxide dismutase have been summarized (28).

Much less is known about manganese superoxide dismutase (MnSOD). The MnSOD of *E. coli* K-12 has recently been cloned and mapped (22). Barra et al. disclose a 196 amino acid sequence for the MnSOD polypeptide isolated from human lever cells (19). Prior art disclosure differ, however, concerning the structure of the MnSOD molecule, particularly whether it has two or four identical polypeptide subunits (19,23). It is clear, however, that the MnSOD polypeptide and the CuZn SOD polypeptide are not homologous (19). The amino acid sequence homologies of MnSODs and FeSOD from various sources have also been compared (18).

Baret et al. disclose in a rat model that the half-life of human MnSOD is substantially longer than the half-life of human copper SOD; they also disclose that in the rat model, human MnSOD and rat copper SOD are not effective as anti-inflammatory agents whereas bovine copper SOD and human copper SOD are fully active (20).

McCord et al., disclosed that naturally occurring human manganese superoxide dismutase protects human phagocytosing polymorphonuclear (PMN) leukocytes from superoxide free radicals better than bovine or porcine CuZn superoxide dismutase in "in vitro" tests (21).

The present invention concerns the preparation of a cDNA molecule encoding the human manganese superoxide dismutase polypeptide or an analog or mutant thereof. It is also directed to inserting this cDNA into efficient bacterial expression vectors, to producing human MnSOD polypeptide, analog, mutant and enzyme in bacteria, to recovering the bacterially produced human MnSOD polypeptide, analog, mutant or enzyme. This invention is also directed to the human MnSOD polypeptides, analogs, or mutants thereof so recovered and their uses.

This invention further provides a method for producing enzymatically active human MnSOD in bacteria, as well as a method for recovering and purifying such enzymatically active human MnSOD.

The present invention also relates to using human manganese superoxide dismutase or analogs or mutants thereof to catalyze the reduction of superoxide radicals to hydrogen peroxide and molecular oxygen. In particular, the present invention concerns using bacterially produced MnSOD or analogs or mutants thereof to reduce reperfusion injury following ischemia and prolong the survival period of excised isolated organs. It also concerns the use of bacterially produced MnSOD or analogs thereof to treat inflammations.

SUMMARY OF THE INVENTION

Figure 1A:
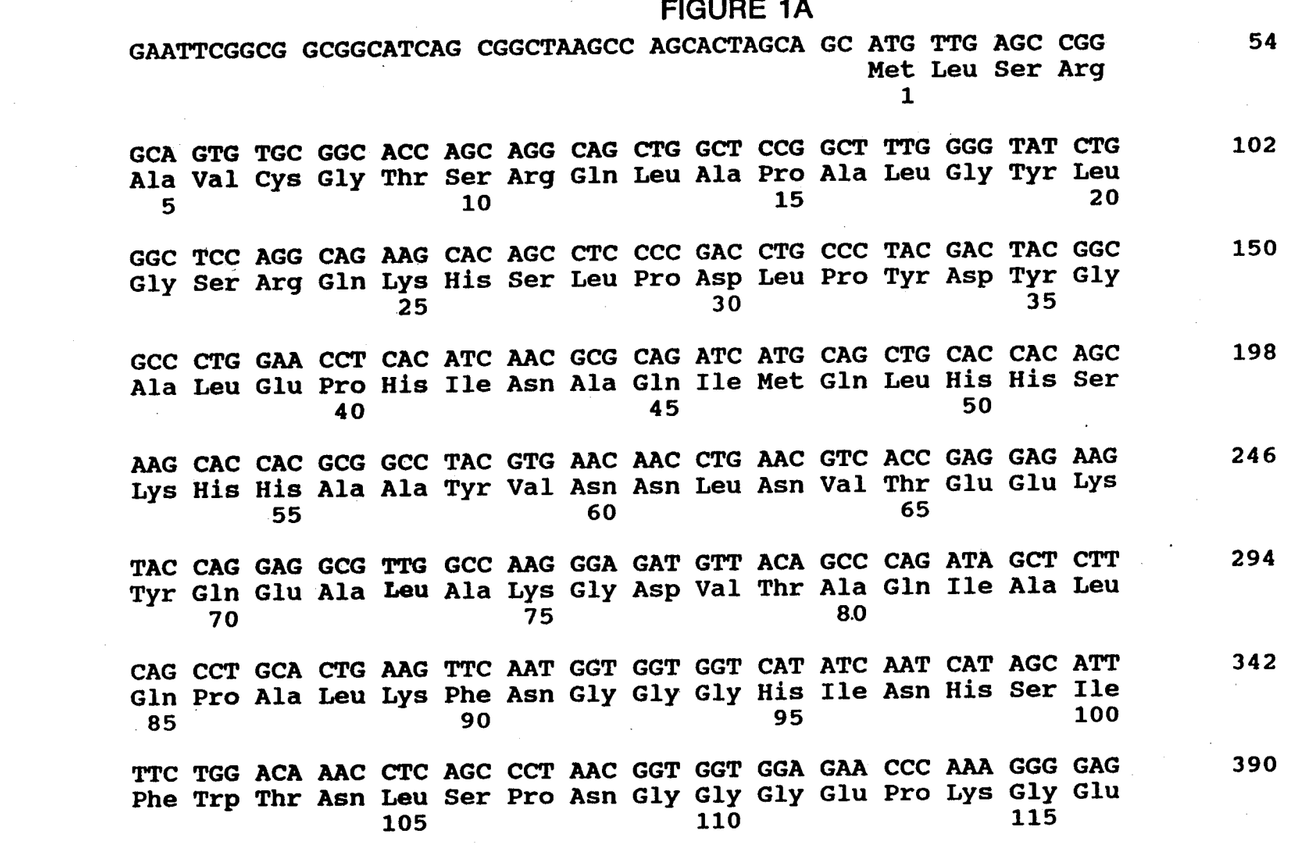
FIG. 1 shows the nucleotide sequence of one strand of a double-stranded DNA molecule encoding the human manganese superoxide dismutase as well as the 198 amino acid sequence of human MnSOD corresponding to the DNA sequence.
Figure 1B:
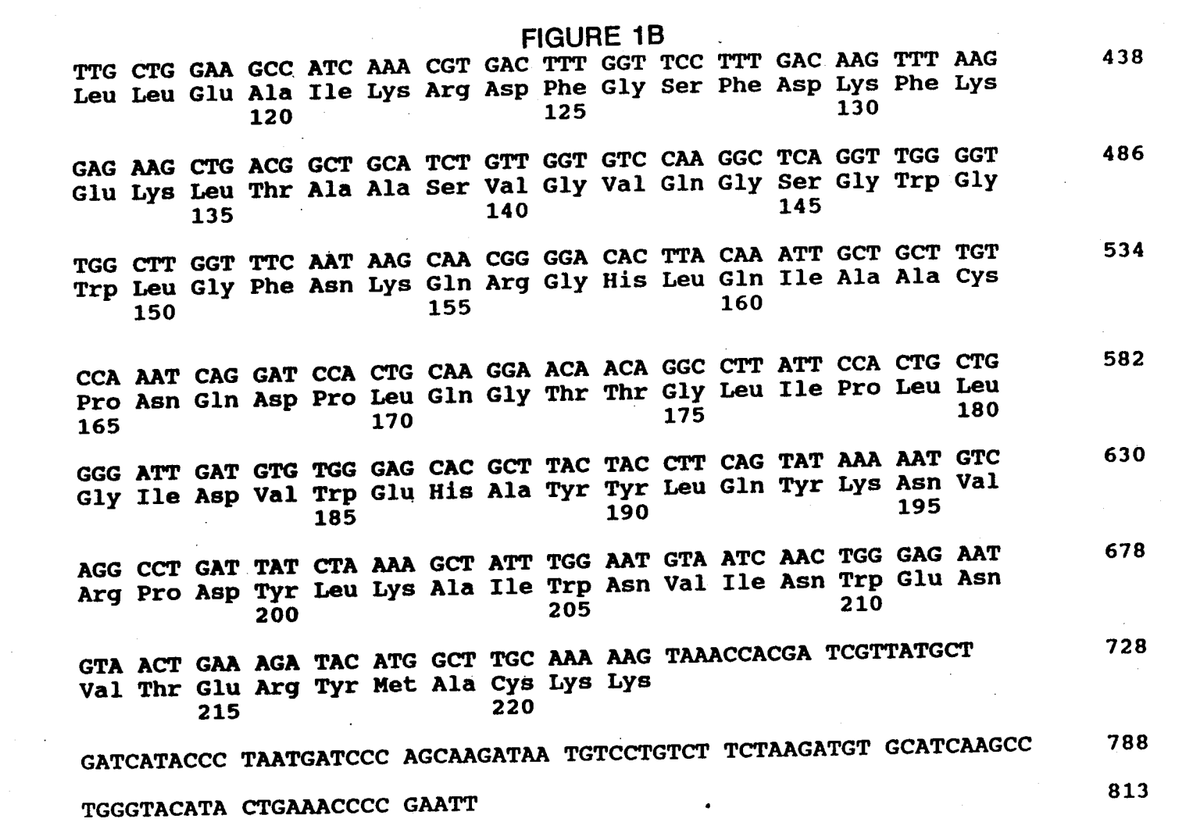

A DNA molecule which includes cDNA encoding the human manganese superoxide dismutase polypeptide or analog or mutant thereof has been isolated from a human T-cell cDNA library. The nucleotide sequence of a double-stranded DNA molecule which encodes human manganese superoxide dismutase polypeptide or analog or mutant thereof has been discovered. The sequence of one strand encoding the polypeptide or analog thereof is shown in FIG. 1 from nucleotide 115 downstream to nucleotide 708 inclusive. Other sequences encoding the analog or mutant may be substantially similar to the strand encoding the polypeptide. The nucleotide sequence of one strand of a double stranded DNA molecule which encodes a twenty-four (24) amino acid prepeptide is also shown in FIG. 1, from nucleotides number 43 through 114, inclusive.

The double-stranded cDNA molecule or any other double-stranded DNA molecule which contains a nucleotide strand having the sequence encoding the human manganese superoxide dismutase polypeptide or analog or mutant thereof may be incorporated into a cloning vehicle such as a plasmid or virus. Either DNA molecule may be introduced into a cell, either procaryotic, e.g., bacterial, or eukaryotic, e.g., yeast or mammalian, using known methods, including but not limited to method involving cloning vehicles containing either molecule.

Figure 4:
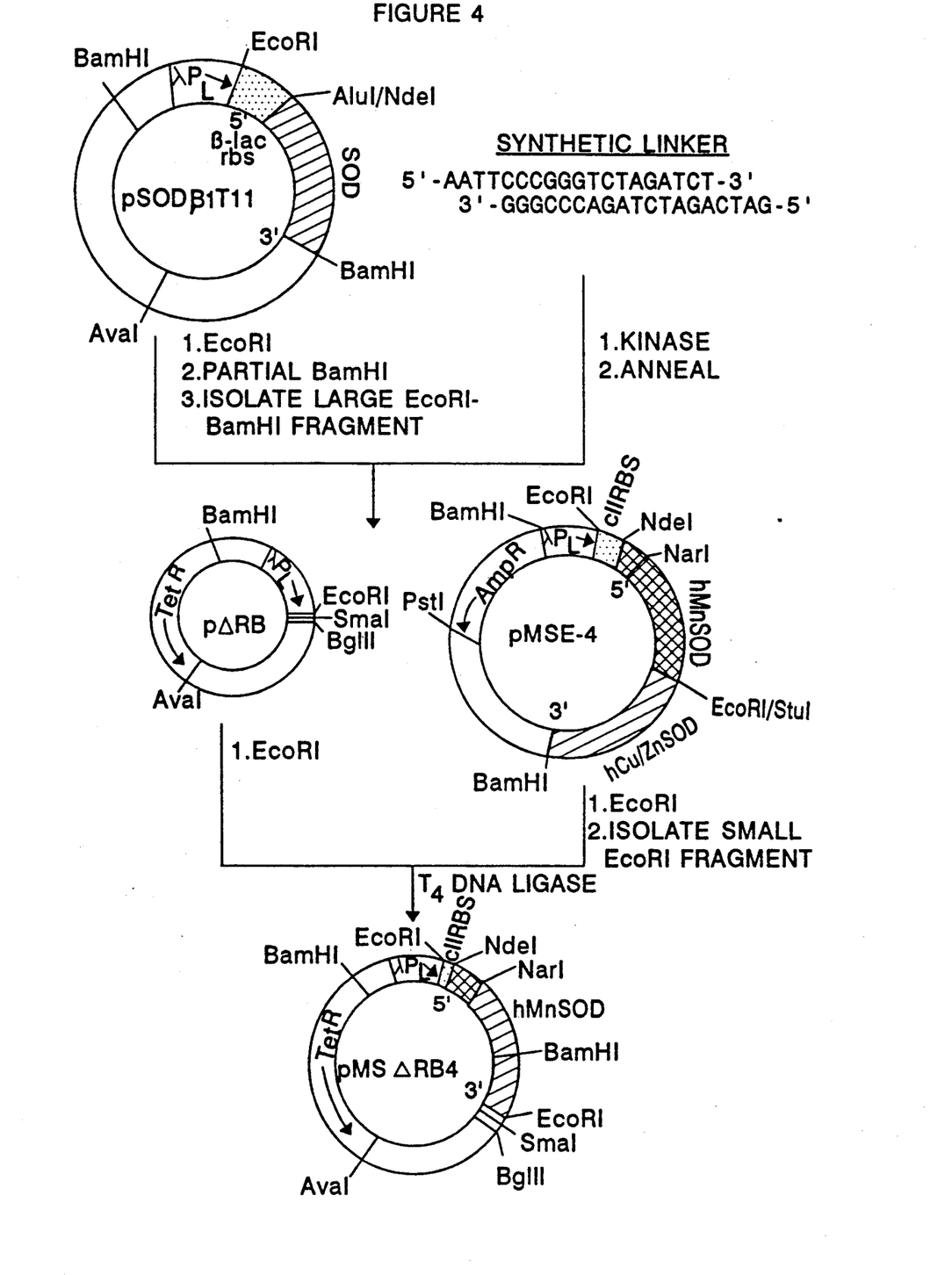

Preferably the cDNA or DNA encoding the human manganese superoxide dismutase polypeptide or analog or mutant thereof is incorporated into a plasmid, e.g., pMSE-4 or pMSΔRB4, and then introduced into a suitable host cell where the DNA can be expressed and the human manganese superoxide dismutase (hMnSOD) polypeptide or analog or mutant thereof produced. Preferred host cells include *Escherichia coli*, in particular *E. coli* A4255 and *E. coli* A1645. The plasmid pMSE-4 in *E. coli* strain A4255 has been deposited with the American Type Culture Collection under ATCC Accession No. 53250. The plasmid pMSΔRB4 may be obtained as shown in FIG. 4 and described in the Description of the Figures.

Cells into which such DNA molecules have been introduced may be cultured or grown in accordance with methods known to those skilled in the art under suitable conditions permitting transcription of the DNA into mRNA and expression of the mRNA as protein. The resulting manganese superoxide dismutase protein may then be recovered.

Veterinary and pharmaceutical compositions containing human MnSOD or analogs or mutants thereof and suitable carriers may also be prepared. This human manganese superoxide dismutase or analogs or mutants may be used to catalyze the following reactions:

and thereby reduce cell injury caused by superoxide radicals.

More particularly, these enzymes or analogs or mutants thereof may be used to reduce injury caused by reperfusion following ischemia, increase the survival time of excised isolated organs, or treat inflammations.

This invention is directed to a method of producing enzymatically active human manganese superoxide dismutase or an analog or mutant thereof in a bacterial cell. The bacterial cell contains and is capable of expressing a DNA sequence encoding the human manganese superoxide dismutase or analog or mutant thereof. The method comprises maintaining the bacterial cell under suitable conditions and in a suitable production medium. The production medium is supplemented with an amount of $Mn^{++}$ so that the concentration of $Mn^{++}$ available to the cell in the medium is greater than about 2 ppm.

In a preferred embodiment of the invention the bacterial cell is an *Escherichia coli* cell containing a plasmid which contains a DNA sequence encoding for the human manganese superoxide dismutase polypeptide e.g. pMSE-4 or pMSΔRB4 in *E. coli* strain A4255. The concentration of $Mn^{++}$ in the production medium ranges from about 50 to about 1500 ppm, with concentrations of 150 and 750 ppm being preferred.

This invention also concerns a method of recovering manganese superoxide dismutase or analog thereof from bacterial cells which contain the same. The cells are first treated to recover a protein fraction containing proteins present in the cells including human manganese superoxide dismutase or analog or mutant thereof and then the protein fraction is treated to recover human manganese superoxide dismutase or analog or mutant thereof. In a preferred embodiment of the invention, the cells are first treated to separate soluble proteins from insoluble proteins and cell wall debris and the soluble proteins are recovered. The soluble proteins are then treated to separate, e.g. precipitate, a fraction of the soluble proteins containing the hMnSOD or analog or mutant thereof and the fraction containing the hMnSOD or analog or mutant is recovered. The recovered fraction of soluble proteins is then treated to separately recover the human manganese superoxide dismutase or analog thereof.

A more preferred embodiment of the invention concerns a method of recovering human manganese superoxide dismutase or analog or mutant thereof from bacterial cells which contain human manganese superoxide dismutase or analog or mutant thereof. The method involves first isolating the bacterial cells from the production medium and suspending them in suitable solution having a pH of about 7.0 to 8.0. The cells are then disrupted and centrifuged and the resulting supernatant is heated for about 30 to 120 minutes at a temperature between 55° and 65° C., preferably for 45-75 minutes at 58°-62° C. and more preferably for 1 hour at 60° C. and then cooled to below 10° C., preferably to 4° C. Any precipitate which forms is to be removed e.g. by centrifugation, and the cooled supernatant is dialyzed against an appropriate buffer e.g. 2 mM potassium phosphate buffer having a pH of about 7.8. Preferably, the dialysis is by ultrafiltration using a filtration membrane smaller than 30K. Simultaneously with or after dialysis the cooled supernatant optionally may be concentrated to an approximate convenient volume e.g. 0.03 of its original volume. The retentate is then eluted on an anion exchange chromatography column with an appropriate buffered solution e.g. a solution of at least 20 mM potassium phosphate buffer having a pH of about 7.8. The fractions of eluent containing superoxide dismutase are collected, pooled and dialyzed against about 40 mM potassium acetate, pH 5.5. The dialyzed pooled fractions are then eluted through a cation exchange chromatography column having a linear gradient of about 40 to about 200 mM potassium acetate and a pH of 5.5. The peak fractions containing the superoxide dismutase are collected and pooled. Optionally the pooled peak fractions may then be dialyzed against an appropriate solution e.g. water or a buffer solution of about 10 mM potassium phosphate buffer having a pH of about 7.8.

The invention also concerns purified enzymatically active human manganese superoxide dismutase or analogs thereof e.g. met-hMnSOD, or mutants produced by the methods of this invention.

BRIEF DESCRIPTION OF THE FIGURES

FIG. 1 (parts A and B)

The Sequence of Human MnSOD cDNA

FIG. 1 also shows the nucleotide sequence of one strand of a double stranded DNA molecule encoding a prepeptide to the mature human MnSOD consisting of twenty-four amino acids and the amino acid sequence corresponding to that DNA sequence. Also shown are parts of the 5' and 3' untranslated sequences.

FIG. 2.

Construction of pMSE-4: Human MnSOD Expression Plasmid

Plasmid pMS8-4, containing MnSOD on an EcoRI (R1) insert, was digested to completion with NdeI and NarI restriction enzymes. The large fragment was isolated and ligated with a synthetic oligomer as depicted in FIG. 2. The resulting plasmid, pMS8-NN contains the coding region for the mature MnSOD, preceded by an ATG initiation codon. The above plasmid was digested with EcoRI, ends were filled in with Klenow fragment of Polymerase I and further cleaved with NdeI. The small fragment harboring the MnSOD gene was inserted into pSODα13 which was treated with NdeI and StuI. pSODα13 may be obtained as described in pending co-assigned U.S. patent application Ser. No. 644,245, filed Aug. 27, 1984 which is hereby incorporated by reference. This generated plasmid pMSE-4 containing the MnSOD coding region preceded by the cII ribosomal binding site and under the control of λ P$_L$ promoter. Plasmid pMSE-4 has been deposited with the American Type Culture Collection under ATCC Accession No. 53250.

FIG. 3

Effect of Mn$^{++}$ Concentration on the Activity of SOD Produced in *E. Coli*

The chart in FIG. 3 shows the correlation between the specific activity in units/mg of recombinant soluble MnSOD produced by *E. coli* strain A4255 containing plasmid pMSE-4 under both non-induction (32° C.) and induction (42° C.) conditions, and the concentration of Mn$^{++}$ (parts per million) in the growth medium.

FIG. 4

Construction of pMS Δ RB4: Human MnSOD Expression Plasmid

Tet$^R$ expression vector, pΔRB, was generated from pSODβ$_1$T-11 by complete digestion with EcoRI followed by partial cleavage with BamHI restriction enzymes. pSODβ$_1$T-11 has been deposited with the American Type Culture Collection (ATCC) under Accession No. 53468. The digested plasmid was ligated with synthetic oligomer resulting in pΔRB containing the λ P$_L$ promoter.

The EcoRI fragment of MnSOD expression plasmid pMSE-4, containing cII ribosomal binding site and the complete coding sequence for the mature enzyme, was inserted into the unique EcoRI site of pΔRB. The resulting plasmid, pMSΔRB4, contains the MnSOD gene under control of λ P$_L$ and cII RBS and confers resistance to tetracycline.

DETAILED DESCRIPTION OF THE INVENTION

A double-stranded DNA molecule which includes cDNA encoding human manganese superoxide dismutase polypeptide or an analog or mutant thereof has been isolated from a human T-cell cDNA library. The nucleotide sequence of a double-stranded DNA molecule which encodes human manganese superoxide dismutase polypeptide or an analog or mutant thereof has been discovered. The sequence of one strand of DNA molecule encoding the human manganese superoxide dismutase polypeptide or analog thereof is shown in FIG. 1 and includes nucleotides numbers 115 to 708 inclusive. The sequence of one strand encoding hMnSOD analog or mutant is substantially similar to the strand encoding the hMnSOD polypeptide. The nucleotide sequence of the prepeptide of human manganese superoxide dismutase is also shown in FIG. 1. Nucleotides numbers 43 through 114 inclusive code for this prepeptide.

The methods of preparing the cDNA and of determining the sequence of DNA encoding the human manganese superoxide dismutase polypeptide, analog or mutant thereof are known to those skilled in the art and are described more fully hereinafter. Moreover, now that the DNA sequence which encodes the human manganese superoxide dismutase has been discovered, known synthetic methods can be employed to prepare DNA molecules containing portions of this sequence.

Conventional cloning vehicles such as plasmids, e.g., pBR322, viruses or bacteriophages, e.g., λ, can be modified or engineered using known methods so as to produce novel cloning vehicles which contains cDNA encoding human manganese superoxide dismutase polypeptide, or analogs or mutants thereof. Similarly, such cloning vehicles can be modified or engineered so that they contain DNA molecules, one strand of which includes a segment having the sequence shown in FIG. 1 for human manganese superoxide dismutase polypeptide or segments substantially similar thereto. The DNA molecule inserted may be made by various methods including enzymatic or chemical synthesis.

The resulting cloning vehicles are chemical entities which do not occur in nature and may only be created by the modern technology commonly described as recombinant DNA technology. Preferably the cloning vehicle is a plasmid, e.g. pMSE-4 or pMS RB4. These cloning vehicles may be introduced in cells, either procaryotic, e.g., bacterial (*Escherichia coli, B. subtilis,* etc.) or eukaryotic, e.g., yeast or mammalian, using techniques known to those skilled in the art, such as transformation, transfection and the like. The cells into which the cloning vehicles are introduced will thus contain cDNA encoding human manganese superoxide dismutase polypeptide or analog or mutant thereof if the cDNA was present in the cloning vehicle or will contain DNA which includes a strand, all or a portion of which has the sequence for human MnSOD polypeptide shown in FIG. 1 or sequence substantially similar thereto if such DNA was present in the cloning vehicle.

*Escherichia coli* are preferred host cells for the cloning vehicles of this invention. A presently preferred auxotrophic strain of *E. coli* is A1645 which has been deposited with the American Type Culture Collection in Rockville, Md., U.S.A. containing plasmid pApoE-Ex2, under ATCC Accession No. 39787. All deposits with the American Type Culture Collection referred to in this application were made pursuant to the Budapest Treaty on the International Recognition of the Deposit of Microorganisms.

A1645 was obtained from A1637 by selection for Gal+ (ability to ferment galactose) as well as loss of tetracycline resistance. It still contains elements of phage λ. Its phenotype is C600 r−m+ gal+ thr− leu− lacZ− b1 (λcI857 ΔH1 ΔBamHI N+).

A1637 was obtained from C600 by inserting transposon containing tetracycline resistance gene into the galactose operon as well as elements of phage λ including those elements responsible for cI repressor synthesis. C600 is available from the American Type Culture Collection, as ATCC Accession No. 23724.

Prototrophic strains of *Escherichia coli* which enable high level polypeptide expresssion even when grown in a minimal media are even more preferred as hosts for expression of genes encoding manganese superoxide dismutase. One presently preferred prototrophic strain is A4255. Strain A4255 containing the plasmid pMSE-4 has been deposited with the American Type Culture Collection (Rockville, Md. 20852), on Sep. 25, 1985 under ATCC Accession No. 53250.

The resulting cells into which DNA encoding human manganese superoxide dismutase polypeptide or analog or mutant thereof has been introduced may be treated, e.g. grown or cultured as appropriate under suitable conditions known to those skilled in the art, so that the DNA directs expression of the genetic information encoded by the DNA, e.g. directs expression of the hMnSOD polypeptide or analog or mutant thereof, and the cell expresses the hMnSOD polypeptide or analog or mutant thereof which may then be recovered.

As used throughout this specification, the term "superoxide dismutase" (SOD) means an enzyme or a polypeptide acting upon superoxide or oxygen-free radicals as receptors, or which catalyze the following dismutation reaction:

$$2O_2^- + 2H^+ \rightarrow O_2 + H_2O_2$$

The term "manganese superoxide dismutase" (MnSOD) as used herein means any superoxide dismutase molecule containing the element manganese, in any of its chemical forms.

The term "human manganese superoxide dismutase polypeptide" as used herein means a polypeptide of 198 amino acids a portion of the amino acid sequence of which is shown in FIG. 1; the N-terminus of the sequence is the lysine encoded by nucleotides 115-117 of FIG. 1 and the COOH terminus of the sequence is the lysine encoded by nucleotides 706-706 of FIG. 1.

The term "polypeptide manganese complex" as used herein means a molecule which includes a human manganese superoxide dismutase polypeptide in a complex with manganese in any of its chemical forms and which has the enzymatic activity of naturally-occurring human manganese superoxide dismutase.

The term "human manganese superoxide dismutase" as used herein means a molecule which includes at least two human manganese superoxide dismutase polypeptides in a complex with manganese in any of its chemical forms and which has the enzymatic activity of naturally-occurring human manganese superoxide dismutase.

The term "human manganese superoxide dismutase polypeptide analog" as used herein means a polypeptide which includes a human manganese superoxide dismutase polypeptide to either or both ends of which one or more additional amino acids are attached.

The term "polypeptide manganese complex analog" as used herein means a molecule which includes a polypeptide manganese complex, the polypeptide portion of which includes one or more additional amino acids attached to it at either or both ends.

The term "human manganese superoxide dismutase analog" as used herein means a molecule that includes at least two polypeptides at least one of which is human manganese superoxide dismutase polypeptide analog, in a complex with manganese in any of its chemical forms, and which has the enzymatic activity of naturally-occurring human manganese superoxide dismutase.

The term "human manganese superoxide dismutase polypeptide mutant" as used herein means a polypeptide having an amino acid sequence substantially identical to that of the human manganese superoxide dismutase polypeptide but differing from it by one or more amino acids.

The term "polypeptide manganese complex mutant" means a molecule which includes a human manganese superoxide dismutase polypeptide mutant in a complex with manganese in any of its chemical forms and which has the enzymatic activity of manganese superoxide dismutase.

The term "human manganese superoxide dismutase mutant" as used herein means a molecule which includes at least two polypeptides at least one of which polypeptides is a human manganese superoxide dismutase polypeptide mutant in a complex with manganese in any of its chemical forms and which has the enzymatic activity of naturally-occurring human manganese superoxide dismutase.

The mutants of hMnSOD polypeptide and hMnSOD which are included as a part of this invention may be prepared by mutating the DNA sequence shown in FIG. 1, the N-ter-minus of which sequence is the lysine encoded by nucleotides 115-117 and the COOH terminus of which sequence is encoded by nucleotides 706-708.

The DNA may be mutated by methods known to those of ordinary skill in the art, e.g. Bauer et al., Gene 37: 73-81 (1985). The mutated sequence may be inserted into suitable expression vectors as described herein, which are introduced into cells which are then treated so that the mutated DNA directs expression of the hMnSOD polypeptide mutants and the hMnSOD mutants.

The enzymatically active form of human manganese superoxide dismutase is believed to be a protein having at least two, and possibly four, identical subunits, each of which has approximately 198 amino acids in the sequence shown in FIG. 1 for human manganese superoxide dismutase, the N-terminus of the sequence being the lysine encoded by nucleotides 115-117 of FIG. 1 and the COOH terminus of the sequence being the lysine encoded by nucleotides 706-708 of FIG. 1. Human MnSOD or analogs or mutants thereof may be prepared from cells into which DNA or cDNA encoding human manganese superoxide dismutase, or its analogs or mutants have been introduced. This human MnSOD or analogs or mutants may be used to catalyze the dismutation or univalent reduction of the superoxide anion in the presence of protons to form hydrogen peroxide as shown in the following equation:

$$2O_2^- + 2H^+ \xrightarrow{\text{human MnSOD}} H_2O_2 + O_2$$

Veterinary and pharmaceutical compositions may also be prepared which contain effective amounts of hMnSOD or one or more hMnSOD analogs or mutant and a suitable carrier. Such carriers are well-known to those skilled in the art. The hMnSOD or analog or mutant thereof of may be administered directly or in the form of a composition to the animal or human subject, e.g., to treat a subject afflicted by inflammations or to reduce injury to the subject by oxygen-free radicals on reperfusion following ischemia or organ transplantation. The hMnSOD or analog or mutant may also be added directly or in the form of a composition to the perfusion medium of an isolated organ, to reduce injury to an isolated organ by oxygen-free radicals on perfusion after excision, thus prolonging the survival period of the organ. Additionally, the hMnSOD or analog or mutant thereof may be used to reduce neurological injury on reperfusion following ischemia and to treat bronchial pulmonary dysplasia.

A method of producing enzymatically active human manganese superoxide dismutase or an analog or mutant thereof in a bacterial cell has also been discovered. The bacterial cell contains and is capable of expressing a DNA sequence encoding the human manganese superoxide dismutase or analog or mutant thereof. The method involves maintaining the bacterial cell under suitable conditions and in a suitable production medium. The production medium is supplemented with an amount of $Mn^{++}$ so that the concentration of $Mn^{++}$ in the medium is greater than about 2 ppm.

The bacterial cell can be any bacterium in which a DNA sequence encoding human manganese superoxide dismutase has been introduced by recombinant DNA techniques. The bacterium must be capable of expressing the DNA sequence and producing the protein product. The suitable conditions and production medium will vary according to the species and strain of bacterium.

The bacterial cell may contain the DNA sequence encoding the superoxide dismutase or analog in the body of a vector DNA molecule such as a plasmid. The vector or plasmid is constructed by recombinant DNA techniques to have the sequence encoding the SOD incorporated at a suitable position in the molecule.

In a preferred of the invention the bacterial cell is an *Escherichia coli* cell. A preferred auxotrophic strain of *E. coli* is A1645. A preferred prototrophic strain of *E. coli* is A4255 The *E. coli* cell of this invention contains a plasmid which encodes for human manganese superoxide dismutase or an analog or mutant thereof.

In a preferred embodiment of this invention, the bacterial cell contains the plasmid pMSE-4. A method of constructing this plasmid is described in the Description of the Figures and the plasmid itself is described in Example 2. This plasmid has been deposited with the ATCC under Accession No. 43250.

In another preferred embodiment of this invention, the bacterial cell contains the plasmid pMSΔRB4. A method of constructing this plasmid is described in the Description of the Figures and the plasmid itself is described in Example 5. This plasmid may be constructed from pSOD$\beta_1$T-11 which has been deposited with the American Type Culture Collection (Rockville, Md. 20852) on Mar. 3, 1986 under Accession No. 53468.

In specific embodiments of the invention, an enzymatically active human manganese superoxide dismutase analog is produced by *E. coli* strain A4255 cell containing the plasmid pMSE-4 and by *E. coli* strain A4255 cell containing the plasmid pMSΔRB4.

The suitable production medium for the bacterial cell can be any type of acceptable growth medium such as casein hydrolystate or LB (Luria Broth) medium, the latter being preferred. Suitable growth conditions will vary with the strain of *E. coli* and the plasmid it contains, for example *E. coli* A4255 containing plasmid pMSE-4 is induced at 42° C. and maintained at that temperature from about 1 to about 5 hours. The suitable conditions of temperature, time, agitation and aeration for growing the inoculum and for growing the culture to a desired density before the production phase as well as for maintaining the culture in the production period may vary and are known to those of ordinary skill in the art.

The concentration of $Mn^{++}$ ion in the medium that is necessary to produce enzymatically active MnSOD will vary with the type of medium used.

In LB-type growth media $Mn^{++}$ concentrations of 150 ppm to 750 ppm have been found effective. It is preferred that in all complex types of growth mediums the concentration of $Mn^{++}$ in the medium is from about 50 to about 1500 ppm.

The specific ingredients of the suitable stock, culture, inoculating and production mediums may vary and are known to those of ordinary skill in the art.

This invention also concerns a method of recovering human manganese superoxide dismutase or analog or mutant thereof from bacterial cells which contain the same. The cells are first treated to recover a protein fraction containing proteins present in the cells including human manganese superoxide dismutase or analog or mutant thereof and then the protein fraction is treated to recover human manganese superoxide dismutase or analog or mutant thereof.

In a preferred embodiment of the invention, the cells are first treated to separate soluble proteins from insoluble proteins and cell wall debris and the soluble proteins are then recovered. The soluble proteins so recovered are then treated to separate, e.g. precipitate, a fraction of the soluble proteins containing the human manganese superoxide dismutase or analog or mutant thereof and the fraction is recovered. The fraction is then treated to separately recover the human manganese superoxide dismutase or analog or mutant thereof.

The following is a description of a more preferred embodiment of the invention. First, the bacterial cells are isolated from the production medium and suspended in a suitable solution having a pH of about 7.0 or 8.0. The cells are then disrupted and centrifuged. The resulting supernatant is heated for a period of about 30 to 120 minutes at a temperature between approximately 55° to 65° C., preferably for 45-75 minutes at 58° to 62° C. and more preferably one hour at 60° C., and then cooled to below 10° C., preferably to about 4° C. Any precipitate which may form during cooling is removed, e.g. by centrifugation and then the cooled supernatant is dialyzed against an appropriate buffer. Preferably the cooled supernatnat is dialyzed by ultrafiltration employing a filtration membrane smaller than 30K, most preferably 10K. Appropriate buffers include 2 mM potassium phosphate buffer having a pH of about 7.8. After or simultaneously with this dialysis the cooled supernatant may optionally be concentrated to an appropriate volume, e.g. 0.03 of the supernatant's original volume has been found to be convenient. The retentate is then eluted on an anion exchange chromatography column with an appropriate buffered solution, e.g., a solution at least 20 mM potassium phosphate buffer having a pH of about 7.8. The fractions of eluent containing superoxide dismutase are collected, pooled and dialyzed against about 40 mM potassium acetate, pH 5.5. The dialyzed pooled fractions are then eluted through a cation exchange chromatography column having a linear gradient of about 40 to about 200 mM potassium acetate (KOAC) and a pH of 5.5. The peak fractions containing the superoxide dismutase are collected and pooled. Optionally the pooled peak fractions may then be dialyzed against an appropriate solution, e.g. water or a buffer solution of about 10 mM potassium phosphate having a pH of about 7.8.

The invention also concerns purified, i.e. substantially free of other substances of human origin, human manganese superoxide dismutase or analogs or mutants thereof produced by the methods of this invention. In particular, it concerns a human manganese superoxide dismutase analog having at least two polypeptides, at least one of which polypeptides has the amino acid sequence shown in FIG. 1, the N-terminus of which sequence is the lysine encoded by nucleotides 115-117 of FIG. 1 and the COOH terminus of which sequence is the lysine encoded by nucleotides 706-708 of FIG. 1 plus an additional methnione residue at the N-terminus (Met-hMnSOD). A preferred embodiment of this invention concerns purified Met-hMnSOD having a specific activity of 3500 units/mg.

EXAMPLES

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems or determining the identity of such polypeptides by activity staining of isoelectric focusing (IEF) gels. Such methods are well-known to those or ordinary skill in the art and are described in numerous publications including by way of example the following:

T. Maniatis, E. F. Fritsch and J. Sombrook, *Molecular Cloning: A Laboratory Manual*, Cold Spring Harbor Laboratory, New York (1982).

J. M. McCord and I. Fridovich, *J. Biol. Chem.* 244:6049-55 (1969).

C. Beauchamp and I. Fridovich, *Anal. Biochem.* 44:276-87 (1971).

EXAMPLE 1

In order to identify MnSOD cDNA clones, mixed oligomer probes were synthesized according to the published amino acid sequence (18,19).

5'-probe - 30 mer sequence from $AA_{15}-AA_{24}$ (18, 19)

```
5'                                              3'
T T G C A T A A T T T G T G C C T T A A T G T G T G G T T C
      T         G         T         G
      G                   G
```

3'-probe - 32 mer sequence from $AA_{179}-AA_{189}$ (19)

```
5'                                                  3'
T C T G T T A C G T T T T C C C A G T T T A T T A C G T T C C A
  G G                                 G G
```

The 5'-probe consisting of 30 nucleotides corresponds to amino acids 15 to 24 of mature MnSOD. The 3'-probe consisting of 32 nucleotides corresponds to amino acids 179 to 189 of mature MnSOD. The 5'-probe is a mixed probe consisting of 36 different sequences, as shown above. The 3'-probe is a mixed probe consisting of 16 different sequences as shown above. (When more than one nucleotide is shown at a given position, the DNA strand was synthesized with equimolar amounts of each of the shown nucleotides thus resulting in the mixed probe).

The 5'-probe was employed to screen 300,000 plaques of a T-cell cDNA library cloned into the λ gt-10 vector. Hybridization to phage plaque replicas immobilized on nitrocellulose filters was performed according to standard procedures (Maniatis et al. supra) except that the hybridization was performed at 50° C. in 8×SSC for 16 hrs. The filters were then washed at 50° C. with 5×SSC and 0.1% SDS. Three positive plaques were isolated and named Phi MS8, Phi MS1 and Phi MS1J.

EcoRI digests of DNA from Phi MS8 and Phi MS1 showed that they both have cDNA inserts approximately 800 bp long, which hybridize to both the 5' and 3' oligonucleotide probes. Phi MS1J carried only 450 bp cDNA insert which hybridized only to the 5' end probe.

The EcoRI inserts of the three phage clones were subcloned into the EcoRI site of pBR322 thus yielding pMS8-4, and pMS1-4 and pMS1J, respectively. Restriction analysis and hybridization to the 5' wd 3' oligonucleotide probes revealed similar patterns for both MS8-4 and pMS1-4. The following restriction map showing the 5'→3' orientation has been deduced for both plasmids.

The sequence of the cDNA insert of pMS8-4 is shown in FIG. 1. The predicted amino acid sequence differs from the published amino acid sequence (19) in the Glu appears instead of Gln in three (3) locations (AA 42, 88, 108) and an additional two amino acids, Gly and Trp appear between $AA_{123-124}$. Sequence analysis of pMS1-4 and pMS1J revealed that the tree MnSOD clones were independently derived and confirmed these differences from the published amino acid sequence.

The sequence upstream of the N-terminal Lysine of mature MnSOD predicts a pre-peptide sequence of 24 amino acids.

EXAMPLE 2

Construction of pMSE-4: $Amp^R$ Human MnSOD Expression Plasmid

Figure 2:
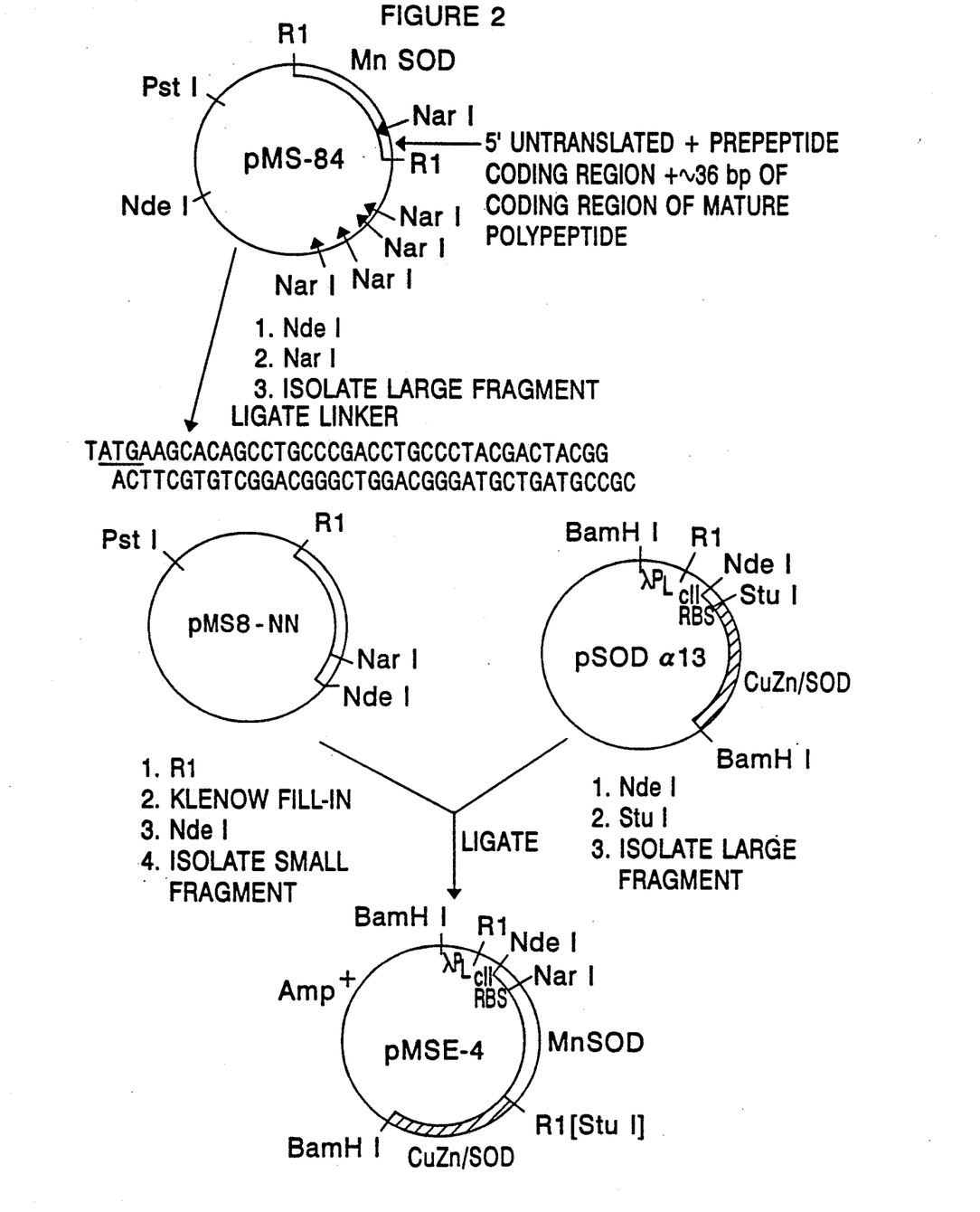

The starting point for the construction of pMSE-4 is the plasmid pMS8-4 which was obtained as described in Example 1. Plasmid pMS8-4, containing human MnSOD cDNA on an EcoRI insert, was digested to completion with NdeI and NarI restriction enzymes. The large fragment was isolated and ligated with a synthetic oligomer as depicted in FIG. 2. The resulting plasmid, pMS8-NN contains the coding region for the mature MnSOD, preceded by an ATG initiation codon. The above plasmid was digested with EcoRI, ends were filled in with Klenow fragment of Polymerase I and further cleaved with NdeI. The small fragment containing the MnSOD gene was inserted into pSODa 13 which was treated with NdeI and StuI. pSODa 13 may be obtained as described in pending, co-assigned U.S. patent application Ser. No. 644,245, filed Aug. 27, 1984 which is hereby incorporated by reference. This generated plasmid pMSE-4 containing the MnSOD coding region preceded by the cII ribosomal binding site and under the control of $\lambda$ $P_L$ promoter. Plasmid pMSE-4 has been deposited with the American Type Culture Collection under ATCC Accession No. 53250. All methods utilized in the above processes are essentially the same as those described in Maniatis, supra.

EXAMPLE 3

Expression of the Recombinant Human MnSOD

Plasmid pMSE-4 was introduced into Escherichia coli strain A4255 using known methods. Then the E. coli strain A4255, containing pMSE-4, were grown at 32° C. in Luria Broth (LB) medium containing 100 ug/ml) of ampicillin until the Optical Density (OD) at 600 nm was 0.7. Induction was performed at 42° C. Samples taken at various time intervals were electrophoresed separated on sodium dodecyl sulfate—polyacrylamide gels electrophoresis (SDS-PAGE). The gels showed increases in human MnSOD levels up to 120 minutes post-induction, at which stage the recombinant MnSOD protein comprised 27% of total cellular proteins as determined by scanning of Coomassie-blue stained gel. Sonication of samples for 90 sec. in a W-375 sonicator and partitioning of proteins to soluble (s) and non-soluble (p) fractions by centrifugation at 10,000 g for 5 min. revealed that most of the recombinant MnSOD produced was non-soluble. The induced soluble protein fraction contained only slightly more SOD activity than the uninduced counterpart, as assayed by standard methods. The standard assay is performed in 3 ml of 0.05M potassium phosphate buffer at pH 7.8 containing $10^{-4}M$ EDTA in a 1.0 cm cuvette thermostatted at 25° C. The reaction mixture contained $1 \times 10^{-5}M$ ferricytochrome c, $5 \times 10^{-5}M$ xanthine, and sufficient xanthine oxidase to produce a rate of reduction of ferricytochrome c at 550 nm of 0.025 absorbance units per minute. The concentration of xanthine oxidase in the cuvette was usually $6 \times 10^{-9}M$ but may vary with different preparations of the enzyme. Under these defined conditions, the amount of superoxide dismutase required to inhibit the rate of reduction of cytochrome c by 50% (i.e. to a rate of 0.0125 absorbance units per minute) is defined as 1 unit of activity. See McCord et al., supra. Apparently a portion of the MnSOD found in the soluble fraction is inactive. This suggested that most of the human MnSOD produced under the conditions described in this Example is, in effect, inactive.

EXAMPLE 4

Effect of $Mn^{++}$ Growth Media on MnSOD Solubility and Activity

Figure 3:
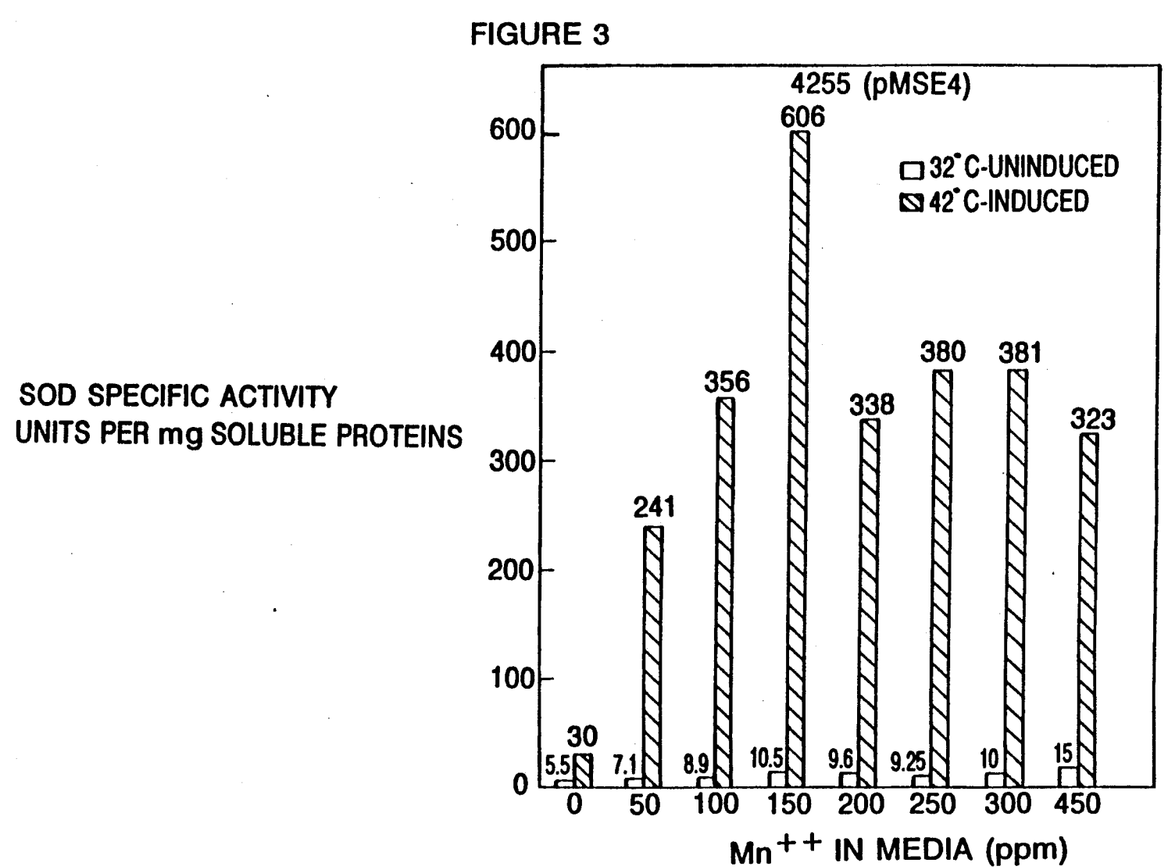

The addition of $Mn^{++}$ in increasing concentrations up to 450 ppm to the growth media of E. coli A4255, containing pMSE-4, prior to a 2 hr. induction at 42° C., at OD 600=0.7, had no adverse effect on the overall yield of human MnSOD. Analysis of sonicated protein fractions soluble (s) and non-soluble (p) on sodium dodecyl sulfate—polyacrylamide gel electrophoresis (SDS-PAGE), showed increased solubilization of the recombinant protein with increased $Mn^{++}$ concentrations (Table 1). An assay of SOD activity (see McCord et al., supra) suggests a correlation between increased $Mn^{++}$ concentrations in the growth media and increased solubility of the MnSOD with an apparent optimum at 150 ppm $Mn^{++}$ concentration in the media (FIG. 3). Furthermore increased $Mn^{++}$ concentrations activated previously inactive soluble enzyme. Soluble protein fractions of induced cultures grown at these $Mn^{++}$ levels show up to 60-fold increase in SOD activity over soluble protein fractions of non-induced cultures grown at these $Mn^{++}$ levels. Activity staining of isoelectric focusing (IEF) gels (see Beauchamp et al, supra.) revealed that multi forms of the recombinant MnSOD were identical to those of native human liver MnSOD.

Results for human MnSOD production by E. coli A1645 containing pMSE-4 were similar to those described above.

TABLE 1

| $Mn^{++}$ (ppm) | Percent Soluble human MnSOD of Total Human MnSOD Induced | Percent Soluble human MnSOD of Soluble Bacterial Proteins | Specific Activity units/mg Soluble Proteins |
| --- | --- | --- | --- |
| 0 | 30.6 | 7.2 | 30 |
| 50 | 72.7 | 15.4 | 241 |
| 100 | 78.0 | 16.9 | 356 |

TABLE 1-continued

| $Mn^{++}$ (ppm) | Percent Soluble human MnSOD of Total Human MnSOD Induced | Percent Soluble human MnSOD of Soluble Bacterial Proteins | Specific Activity units/mg Soluble Proteins |
|---|---|---|---|
| 150 | 82.9 | 18.8 | 606 |
| 200 | 82.0 | 20.8 | 338 |
| 250 | 79.2 | 20.4 | 380 |
| 300 | 80.8 | 20.3 | 381 |
| 450 | 89.2 | 22.4 | 323 |

EXAMPLE 5

Construction of pMSΔRB4: $Tet^R$ Human MnSOD Expression Plasmid $Tet^R$ expression vector, pΔRB, was generated from pSODβ₁T-11 by complete digestion with EcoRI followed by partial cleavage with BamHI restriction enzymes. pSODβ₁T-11 has been deposited with the American Type Culture Collection under Accession No. 53468. The digested plasmid was ligated with synthetic oligomer resulting in pΔRB containing the λ $P_L$ promoter.

The EcoRI fragment of MnSOD expression plasmid pMSE-4, containing cII ribosomal binding site and the complete coding sequence for the mature enzyme, was inserted into the unique EcoRI site of pΔRB. The resulting plasmid, pMSΔRB4, contains the MnSOD gene under control of λ $P_L$ and cII RBS and confers resistance to tetracycline (FIG. 4).

EXAMPLE 6

Expression of Human MnSOD from pMSΔRB4

Plasmid pMSΔRB4 was introduced into *Escherichia coli* strain A4255, using known methods. Cultures were grown at 32° C. in Luria Broth (LB) containing various concentrations of $Mn^{++}$, until the Optical Density (OD) at 600 nm reached 0.7. Induction was performed at 42° C. Samples taken at various time intervals were electrophoresed on SDS-PAGE. hMnSOD level increased with induction time up to 120 minutes, at which stage it comprised about 15% of total celluar proteins as determined by scanning of Coomassie Blue stained gel.

The induced MnSOD was soluble, regardless of $Mn^{++}$ concentration in growth media. This is in contrast with observations for the $Amp^R$ plasmid pMSE-4. (See Example 4.) However, maximum SOD activity and expression level were dependent on $Mn^{++}$ supplementation (Table 2).

TABLE 2

| MnSOD Expression in E. Coli A4255 (pMS ΔRB4) | | | |
|---|---|---|---|
| | Percent Soluble hMnSOD of Soluble Bacterial Proteins | Specific Activity Units/ mg Soluble Proteins | |
| ppm $Mn^{++}$ | 42° | 32° | 42° |
| 0 | 10.9 | 8.0 | 23 |
| 50 | 19.8 | 8.0 | 227 |
| 100 | 16.0 | 8.0 | 241 |
| 200 | 17.0 | 10.0 | 278 |
| 300 | 16.0 | 9.3 | 238 |

EXAMPLE 7

Purification of Enzymatically Active Recombinant Human MnSOD

*E. coli* strain A4255 harboring plasmid pMSΔRB4 was fermented in LB supplemented with 750 ppm $Mn^{++}$, at 32° C. to an OD600 of 17.0. Induction of human MnSOD expression was effected by a temperature shift to 42° C. for 2 hours at which stage the culture reached OD600 of 43.0. Cells were harvested by centrifugation and resuspended in 0.2 original volume in 50 mM potassium phosphate buffer, pH 7.8 containing 250 mM NaCl. Bacteria were disrupted by a double passage through Dynomill, centrifuged and cell debris were discarded. The supernatant was heated for 1 hour at 60° C., cooled to 4° C. and the cleared supernatant was concentrated to 0.03 original volume and dialyzed against 2 mM potassium phosphate buffer, pH 7.8, on a Pellicon ® ultra filtration unit equipped with a 10K membrane. The crude enzyme preparation was loaded onto a DE52 column, washed thoroughly with 2 mM potassium phosphate buffer, pH 7.8 and eluted with 20 mM potassium phosphate buffer, pH 7.8. Pooled fractions containing the enzyme were dialyzed against 40 mM potassium acetate, pH 5.5, loaded onto a CM52 column and eluted with a linear gradient of 40-200 mM potassium acetate, pH 5.5. Peak fractions containing human MnSOD were pooled, dialyzed against $H_2O$, adjusted to 10 mM potassium phosphate buffer, pH 7.8 and frozen at $-20°$ C.

Recombinant human MnSOD obtained was more than 99% pure, with a specific activity of about 3500 units/mg. The overall yield of the purification procedure was about 30% (Table 3).

Sequencing of the purified enzyme shows the presence of an additional methionine at the N-terminal amino acid as compared with the known human MnSOD (19).

Analysis for metal content by atomic absorption revealed about 0.77 atoms Mn per enzyme subunit. This is in accordance with published data (23).

TABLE 3

| Purification of Recombinant Human* Mn-SOD | | | |
|---|---|---|---|
| | Total Proteins | Yield | Specific Activity |
| Step | gm | gmSOD | % | units/mg |
| Dynomill supernatant | 100.0 | 11.9 | 100.0 | 417 |
| 60° C. supernatant | 24.0 | 8.2 | 68.9 | 1197 |
| Pelicon retentate | 20.0 | 7.5 | 63.0 | 1350 |
| DE52 eluate | 7.3 | 5.7 | 48.0 | 2732 |
| CM52 eluate | 4.2 | 4.2 | 35.3 | 3500 |

*Values for enzyme purified from 15 L fermentation.

REFERENCES

1. McCord, J. M. and Fridovich, I., *J. Biol. Chem.* 244:6049-55 (1969).
2. Fridovich, I. in *Advances in Inorganic Biochemistry*, eds. Eichhorn, G. L. and Marzilli, L. G. (Elsevier/-North Holland, New York), pp. 67-90 (1979).
3. Freeman, B. A. and Crapo, J. D., *Laboratory Investion* 47:412-26 (1982).
4. Steinman, H. M. in *Superoxide Dismutase*, ed. Oberley, L. W. (CRC Press, Fla.), pp. 11-68 (1982).
5. Hartz, J. W. and Deutsch, H. F., *J. Biol. Chem.* 247:7043-50 (1972).

6. Jabusch, J. R., Farb, D. L., Kerschensteiner, D. A. and Deutsch, H. F., *Biochemistry* 19:2310-16 (1980).
7. Barra, D., Martini, F., Bannister, J. V., Schinina, M. W., Rotilio, W. H., Bannister, W. H. and Bossa, F., *FEBS Letters* 120:53-56 (1980).
8. Lieman-Hurwitz, J., Dafni, N., Lavie, V. and Groner, Y., *Proc. Natl. Acad. Sci. USA* 79:2808-11 (1982).
9. Sherman, L., Dafni, N., Lieman-Hurwitz, J. and Groner, Y., *Proc. Natl. Acad. Sci. USA* 80:5465-69 (1983).
10. Oberley, L. W. and Buettner, G. R., *Cancer Research* 39:1141-49 (1979).
11. Huber, W. and Menander-Huber, K. B., *Clinics in Rheum. Dis.* 6:465-98 (1980).
12. McCord, J. M. and Roy, R. S., *Can. J. Physiol. Pharma.* 60:1346-52 (1982).
13. Alvarez, J. G. and Storey, B. T., *Biol. Reprod,* 28:1129-36 (1983).
14. Talmasoff, J. M., Ono, T. and Cutler, R. G., *Proc. Natl. Acad. Sci. USA* 77:2777-81 (1980).
15. Lowry, O. H., Rosebrough, N. J., Farr, A. L. and Randall, R. J., *J. Biol. Chem.* 193:265-75 (1951).
16. Weser, U. and Hartmann, H. J., *FEBS Letters* 17:78-80 (1971).
17. Jewett, S. L., Latrenta G. S. and Beck, C. M., *Arc. Biochem. Biophys.* 215: 116-128 (1982).
18. Harris, J. I. and Steinman, H. M., *Superoxide and Superoxide Dismutase,* Michelson, A. M., McCord, J. M. and Fridovich, I. eds., Academic Press, London, pp. 225-230 (1977).
19. Barra, D., Schinina, M. E., Simmaco, M., Bannister, J. V., Bannister, W. H., Rotilio, G. and Bossa, F., *J. Biol. Chem.* 259:12595-601 (Oct. 25, 1984).
20. Baret, A., Jadot, G., and Michelson, A. M., *Biochemical Pharmacology* 33:2755-60 (Sep. 1, 1984).
21. McCord J. M. and Salin, M. L., *Movement, Metabolism and Bactericidal Mechanisms of Phagocytes,* Ross, A., Patriarca, P. L., Romeo, D. (eds) pp. 257-264 (1977).
22. Touati, D., *Journal of Bacteriology* 155:1078-87 (1983).
23. McCord, J. M., Boyle, J. A., Day, Jr., E. D., Rizzolo, L. J. and Salin, M. L., *Superoxide and Superoxide Dismutase,* Michaelson, A. M., McCord, J. M., and Fridovich, I. (eds) Academic Press, London pp. 129-138 (1977).
24. European Patent Publication No. 0131843 A1, published Jan. 23, 1985, corresponding to European Patent Application No. 84107717.5, filed Jul. 3, 1984, which claims priority of U.S. Ser. No. 514,188, filed Jul. 15, 1983.
25. Hallewell, et al., *Nucleic Acids Res.* 5, (1985).
26. European Patent Publication 0138111 A1, published Apr. 24, 1985, corresponding to European Patent Application No. 84111416.8, filed Sep. 25, 1984, which claims priority of U.S. Ser. No. 538,607, filed Oct. 3, 1983, and U.S. Ser. No. 609,412, filed May 11, 1984.
27. EMBO Journal, vol. 4, No. 1, pp. 77-84 (January 1985).
28. Abstracts of the Fourth International Conference on Superoxide and Superoxide Dismutase, Rome, Italy, Sep. 1-6, 1985.

What is claimed is:

1. A polypeptide consisting of 199 amino acids, the sequence of which has methionine at its N-terminus immediately adjacent to the lysine encoded by nucleotides 115-117 of FIG. 1 and continuing to the lysine encoded by nucleotides 706-708 of FIG. 1 which is the COOH terminus of the polypeptide.

2. An analog of human manganese superoxide dismutase consisting essentially of at least two non-covalently linked identical polypeptides, each such polypeptide consisting of 199 amino acids, the sequence of each such polypeptide having methionine at its N-terminus immediately adjacent to the lysine encoded by nucleotides 115-117 of FIG. 1 and continuing to the lysine encoded by nucleotides 706-708 of FIG. 1 which is the COOH terminus of the polypeptide, which analog has the enzymatic activity of naturally-occurring, human manganese superoxide dismutase.

3. A composition comprising a pharmaceutically acceptable carrier and the human manganese superoxide dismutase analog of claim 2 free of other proteins of human origin.

4. A complex comprising the human manganese superoxide dismutase analog of claim 2 and divalent manganese ($Mn^{+2}$) complexed therewith, which complex has the enzymatic activity of naturally-occurring, human manganese superoxide dismutase.

5. The complex of claim 4 having a specific activity greater than 417 units/mg.

* * * * *